（12) United States Patent
Stoffel et al.

(10) Patent No.: US 9,629,690 B2
(45) Date of Patent: Apr. 25, 2017

(54) SONOTRODE FOR THE INTRODUCTION OF ULTRASONIC ENERGY

(75) Inventors: Marco Stoffel, Zürich (CH); Uwe Werner, Utikon (CH)

(73) Assignee: NEXILIS AG, Grenchen (CH)

( * ) Notice: Subject to any disclaimer, the term of this patent is extended or adjusted under 35 U.S.C. 154(b) by 722 days.

(21) Appl. No.: 14/004,329

(22) PCT Filed: Feb. 2, 2012

(86) PCT No.: PCT/EP2012/051768
§ 371 (c)(1),
(2), (4) Date: Nov. 4, 2013

(87) PCT Pub. No.: WO2012/123182
PCT Pub. Date: Sep. 20, 2012

(65) Prior Publication Data
US 2014/0051035 A1 Feb. 20, 2014

(30) Foreign Application Priority Data

Mar. 11, 2011 (CH) .......................... 419/11

(51) Int. Cl.
*A61C 1/07* (2006.01)
*B06B 3/00* (2006.01)
(Continued)

(52) U.S. Cl.
CPC .................. *A61C 1/07* (2013.01); *A61C 3/03* (2013.01); *A61C 8/0089* (2013.01); *A61N 7/00* (2013.01); *B06B 3/00* (2013.01); *G10K 11/18* (2013.01)

(58) Field of Classification Search
CPC ........... A61C 1/07; A61C 3/03; A61C 8/0089; A61N 7/00; B06B 3/00; G10K 11/18
See application file for complete search history.

(56) References Cited

U.S. PATENT DOCUMENTS

| 5,100,321 A | 3/1992 | Coss et al. |
| 5,899,693 A | 5/1999 | Himeno et al. |

(Continued)

FOREIGN PATENT DOCUMENTS

| DE | 201 13 692 U1 | 11/2001 |
| EP | 0 535 542 A1 | 4/1993 |

(Continued)

*Primary Examiner* — Heidi M Eide
(74) *Attorney, Agent, or Firm* — Sugrue Mion, PLLC

(57) ABSTRACT

A description is given of a sonotrode (18) for connection to an ultrasonic vibration transducer (2, 3) comprising a connecting portion (4), which extends along a first axis (16) and is attached by a first end (42) to the vibration transducer (2, 3) or is connected thereto, wherein the connecting portion (4) is made to vibrate almost exclusively along the first axis (16) by the ultrasonic vibration transducer (2, 3). Said sonotrode is characterized in that, at the free end (43) of the connecting portion (4), opposite from the first end (42), both a substantially cylindrical, first sleeve (5), which extends along a second axis (8), and a substantially cylindrical, second sleeve (6), which extends along a third axis (17), are arranged in a common crossing region (36), wherein the first axis (16) forms a first angle (γ) in the range of 100-140° with the second axis (8), and wherein the first axis (16) forms a second angle (β) in the range of 100-140° with the third axis (17), wherein the three axes (8, 16, 17) are arranged substantially in one sonotrode plane (41). Moreover, corresponding sonotrode tools and uses of such sonotrode tools are described.

25 Claims, 3 Drawing Sheets

(51) Int. Cl.
*A61C 3/03* (2006.01)
*A61C 8/00* (2006.01)
*A61N 7/00* (2006.01)
*G10K 11/18* (2006.01)

(56) References Cited

U.S. PATENT DOCUMENTS

| | | |
|---|---|---|
| 2003/0157458 A1 | 8/2003 | Buchanan |
| 2004/0112547 A1 | 6/2004 | Tamamoto |
| 2006/0253050 A1 | 11/2006 | Yoshimine et al. |
| 2008/0132927 A1 | 6/2008 | Sakai |
| 2009/0042165 A1* | 2/2009 | Garrison ............ A61C 3/08 433/164 |
| 2009/0047623 A1 | 2/2009 | Lesage |
| 2010/0130867 A1 | 5/2010 | Vercellotti et al. |
| 2010/0179654 A1 | 7/2010 | Mayer et al. |

FOREIGN PATENT DOCUMENTS

| | | |
|---|---|---|
| EP | 0 594 541 A2 | 4/1994 |
| EP | 1 530 953 A1 | 5/2005 |
| JP | 63-37923 A | 2/1988 |
| WO | 2005/009256 A2 | 2/2005 |
| WO | 2007/101362 A2 | 9/2007 |
| WO | 2009/141252 A1 | 11/2009 |

* cited by examiner

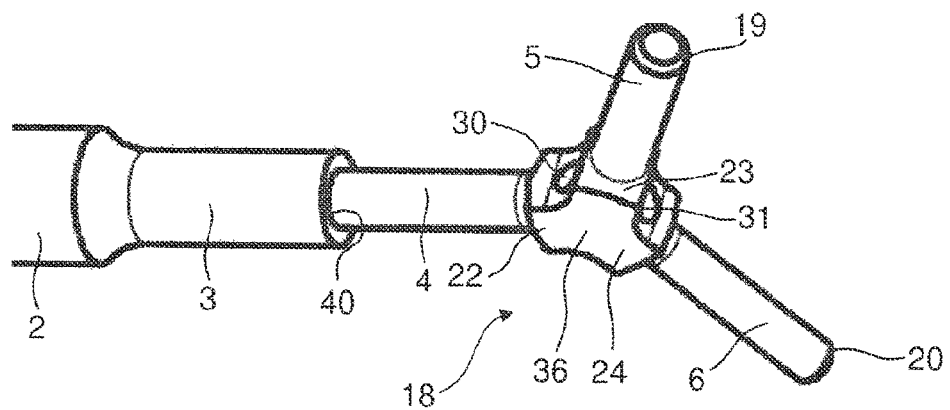
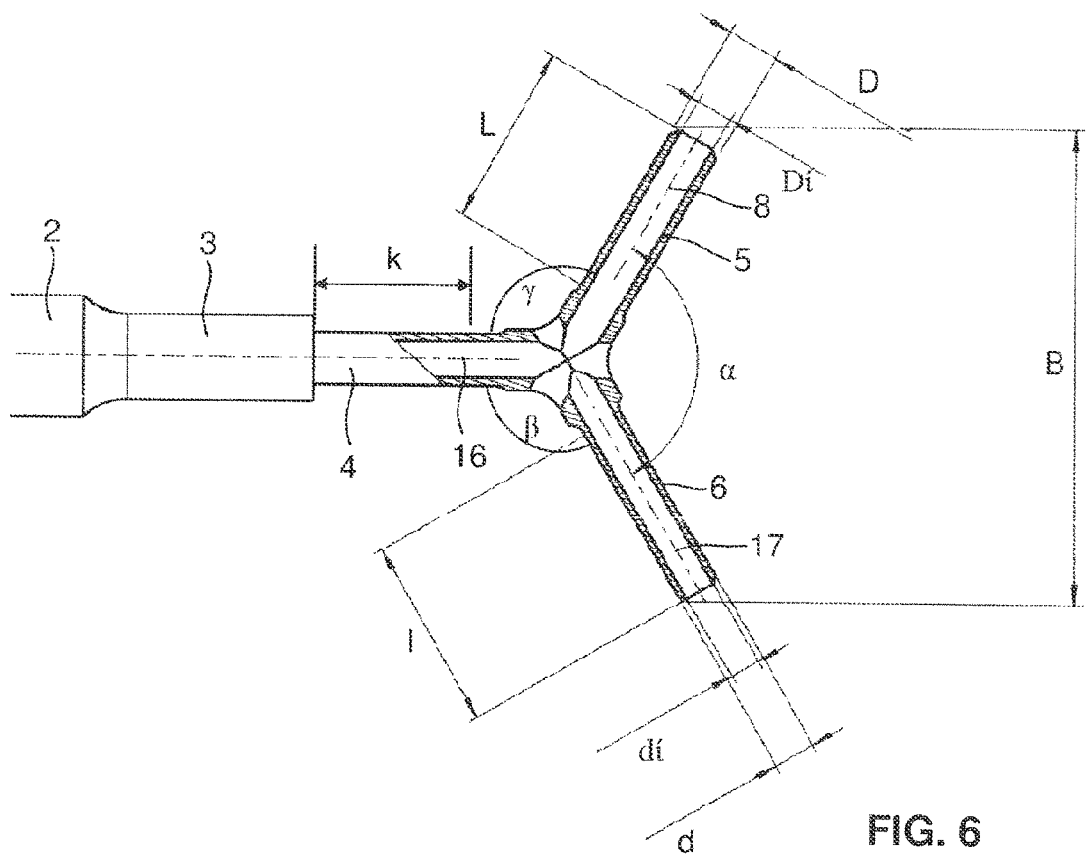
FIG. 5
FIG. 6

SONOTRODE FOR THE INTRODUCTION OF ULTRASONIC ENERGY

CROSS REFERENCE TO RELATED APPLICATIONS

This application is a National Stage of International Application No. PCT/EP2012/051768 filed Feb. 2, 2012, claiming priority based on Swiss Patent Application No. 00419/11, filed Mar. 11, 2011, the contents of all of which are incorporated herein by reference in their entirety.

TECHNICAL FIELD

The present invention relates to sonotrodes for the introduction of ultrasonic energy, especially in porous recesses, to sonotrode tools with such sonotrodes as well as to uses of such devices.

STATE OF THE ART

Ultrasound is increasingly used to obtain connections between workpieces whereby material liquefying itself under ultrasonic action is introduced into a connection point, this is liquefied under ultrasound, and subsequently a positive and/or material-fit connection is established between two workpieces.

For the liquefaction to take place efficiently, i.e. using as little vibration energy as possible, and as localized as possible, it is necessary to provide devices which make it possible to introduce the ultrasonic vibrations at an optimum orientation for the requested application. In addition, it is also important to meet the often difficult space conditions at the introduction point by implementing a deflection of the vibrations.

Accordingly, there is, in the medical as well as in the non-medical area, a large number of special devices known as sonotrode tools which allow the introduction of ultrasound.

Here, as, for example, in U.S. Pat. No. 5,100,321, US 2003/0157458, EP 0535542 or U.S. Pat. No. 5,899,693, respectively EP 1530953, a deflection of ultrasound in the application area, in so far as one can even speak in these cases of an actual targeted deflection of ultrasound, is ensured by coupling on a device generating during ultrasound a sonotrode which has a hook-like shape, with which then, adapted to the narrow space conditions, the vibration energy can be carried specifically to the desired location over the tip of this hook-like device. A problem with such devices is that the deflection of ultrasonic vibrations is a complex matter, and accordingly such devices, when, for example, an ultrasonic vibration is applied in the axial direction at the coupling point, cannot ensure that even at the tip of the sonotrode at an angle to this coupling point an ultrasonic vibration is also applied only along the axis of the tip. Thus at the tip, among other things, lateral vibrations arise, which are extremely undesirable, for example especially in the medical area, because on the one hand during the processing they can lead to unpleasant pain for the patient, but also because they may possibly cause sustainable damages to the surrounding tissue. In addition, this results in an inefficient energy input and thus an undesirable extension of the treatment time.

There are, on the other hand, devices specifically having the purpose to divert ultrasonic vibrations. This is done through bending vibrations of suitably specifically designed sonotrodes, in other words, an axial vibration, which is applied at the foot and along the fastening axis of the sonotrode, is converted to a bending vibration in a normally for this purpose specifically curved intermediate element of the sonotrode, and then at the end of the sonotrode this coupling element performing a bending vibration is transferred in a tip which is geometrically arranged so that at the tip an axial ultrasonic vibration is applied in this tip element in a targeted manner. Devices of this type, which usually have annular or circular intermediate elements taking over the bending vibration, are known for example from EP 0594541, WO 2005/009256, US 2010/0130867 or from DE 20113692.

Such devices have the disadvantage that the curved intermediate elements performing the bending vibration are complex, in particular highly stressed elements, thus being prone to wear, and also requiring a lot of space. One construction based on the same principle is known from WO 2007/101362, but here no truly ring-shaped bending vibration intermediate element is used, rather only a curved bending vibration element in the form of a partial circle.

DESCRIPTION OF THE INVENTION

Accordingly, it is the object of the present invention to provide an improved sonotrode, in particular one which is able to specifically redirect a deflection of oscillating ultrasonic vibrations along only one axis in a small space at a certain angle, i.e., so that oscillating ultrasonic vibrations along the second axis substantially result only along this second axis.

In concrete terms, the object of the invention is to propose a sonotrode for connection to an ultrasonic vibration transducer comprising a connecting portion, which extends along a first axis and is attached by a first end to the vibration transducer or is connected thereto, wherein the connecting portion is made to vibrate substantially exclusively along the first axis by the ultrasonic vibration transducer.

This object is achieved by the features of claim 1.

More specifically, a sonotrode, as proposed herein, is characterized in that, at the free end of the connecting portion, opposite from the first end, both a substantially cylindrical first sleeve, which extends along a second axis, and a substantially cylindrical second sleeve, which extends along a third axis, are arranged in a common crossing region, wherein the first axis forms a first angle in the range of 100-140° with the second axis, and wherein the first axis forms a second angle in the range of 100-140° with the third axis, and wherein the three axes are arranged substantially in one sonotrode plane.

Typically, the first and the second sleeve preferably have a circular cylindrical design, but they can also have a different cross-sectional surface, for example an oval or a polygonal cross-sectional surface. The connecting portion may also have a circular cylindrical design, but it can also have a different cross-sectional surface, for example a rectangular cross-sectional surface or any other polygonal or oval cross-sectional surface.

A core aspect of the invention is the fact that, in contrast to the complicated deflection devices according to the prior art, which typically use bending vibrations for the deflection of a first direction to a second direction (which requires appropriate major elements able to withstand this bending vibration), here a Y-shaped structure is used, which is designed with respect to mass distribution and geometric configuration in such a way that along all the arms ultrasonic vibrations are applied substantially only along the axis of each arm. In other words, a balanced structure is provided, which allows a targeted deflection of the ultrasonic vibrations in the axial direction in a small space. Preferably, in the arms, particularly at the tip of the sleeve, in the case of a hollow cylindrical configuration of the same at the encircling edge, that is at the tip of each sleeve in the area of the front opening, the proportion of vibrations which are not axial (i.e. bending vibrations in the arm or around the crossing point) is not more than 15%, preferably not more than 10%, and especially not more than 5% of the entire ultrasonic vibration energy.

That is, the majority of the vibration energy, i.e. more than 85%, preferably more than 90%, particularly preferably more than 95%, and most preferably at least 98% of the ultrasonic vibration energy in each of the arms, particularly at the tip of the sleeve, in the case of a hollow cylindrical configuration of the same at the encircling edge, i.e. at the tip of each sleeve in the area of the front opening, is applied as axial vibration.

According to a first preferred embodiment, the ratio of outside diameter to the length extending along the second axis, respectively the third axis lies in the range of 1:2-1:10, preferably in the range of 1:3-1:6 for the two sleeves. It is found that with such a dimensioning of the two sleeves, which substantially divide the axial vibration along the connecting portion symmetrically in two different spatial directions, wherein again in these two different spatial directions axial vibrations are present, these ratios can ensure well the above-mentioned mass distribution. It shows in particular that at ratios below 1:2 this results in an unsatisfactory vibration behavior, and that at ratios above 1:10 the corresponding sleeve is too long and starts flapping. Moreover, the connecting portion is preferably designed with a similar length as the two sleeves in order to further optimize the mentioned symmetry. Possible detailed dimensions are outlined further below.

To ensure the mentioned symmetry and the optimal distribution of the vibrations, the first angle $\gamma$ and/or the second angle $\beta$ is preferably in the range of 110-130°, preferably in the range of 115-125°, in particular preferably in the range of 118-122°. Particularly preferred are the two angles substantially 120° so that there is a symmetric element with a threefold rotation axis.

According to a further preferred embodiment, the first angle $\gamma$ and the second angle $\beta$ are equal, up to a deviation of not more than 5°, preferably of not more than 2°. Most preferably, the two angles are substantially exactly the same.

According to a further preferred embodiment, the second axis and the third axis form a third angle $\alpha$, which is in the range of 100-140°, in particular in the range of 110-130°, particularly preferably in the range of 105-125°.

Preferably, both the first sleeve and the second sleeve are designed as a circular cylinder having a circular cylindrical outer surface. Furthermore preferably also the connecting portion is designed as circular cylinder.

Furthermore preferably the outside diameter D of the first sleeve is greater than the outside diameter d of the second sleeve. It is therefore possible to use the two sleeves for different recesses, thus obtaining a tool which ensures, through its symmetrical configuration, an optimum deflection of the ultrasonic vibrations in two directions and along the axes without lateral vibrations, wherein at the same time the two sleeves can be used for the actual working steps, and therefore not just one of the sleeves is provided for the purpose of balancing the deflection of the ultrasonic vibrations. Moreover, the two sleeves can be specifically used for different applications. Preferably, the large diameter is 1.1-3 times, particularly preferably 1.2-2 times larger than the small diameter.

According to a further preferred embodiment, the ratio of outside diameters d, D to the lengths l, L extending along the second axis respectively the third axis, is substantially equal for the two sleeves, to ensure the most efficient mass distribution again.

A further particularly preferred embodiment is characterized in that the first sleeve and/or the second sleeve, and preferably both, have a central axial cylindrical recess which is open to the respective free end to form a front opening. In other words, the two sleeves are configured as a hollow cylinder, but may also be configured as a solid cylinder.

Thus, such a sonotrode can be used in a process like that disclosed in WO 2009/141252. It is also possible to provide one of the sleeves as a hollow cylinder and one as a solid cylinder. If one (or both) sleeves are configured as a solid cylinder, it takes over the function of the guide pin in the method according to WO 2009/141252, if one (or both) sleeves are configured as hollow cylinder, and this is the preferred option, then it is used as a sleeve in terms of the method according to WO 2009/141252. If a hollow cylinder is configured in each case, the thus formed cylindrical interior space preferably has a constant cross-sectional surface over the length. It is also possible to configure only one of the sleeves as a hollow cylinder, and to configure the other sleeve, for example, as a solid cylinder, as short and thus as space-saving as possible, but of such geometry and mass to adjust the vibration characteristics in the hollow sleeves so that only axial vibrations are applied there.

Preferably, the encircling edge formed in the area of this front opening of the respective sleeve is designed preferably conically tapered towards the tip, that is, at the inner edge, the diameter of which corresponds in the inside diameter of the hollow cylinder, there is a preferably sharp edge. Conically tapered can be in terms of a stepped shape, a shape in an axial sectional view taken along a line, or even concavely conically. This is again to optimize the use in conjunction with a method according to WO 2009/141252, in other words, to provide a collar liquefiable by ultrasound applied around a guide pin in the method which penetrates into the porous wall structure of the recess to be ameliorated.

According to a further preferred embodiment, the recess defined inside the hollow cylinder is a through-bore with constant inside diameter along the entire length, which is also accessible at the respective position of the crossing region through a respective rear opening, so that a guide pin with an appropriate outside diameter can be inserted both from the front and from the back or pushed through completely.

A further preferred embodiment is characterized in that both the connecting portion and the two sleeves are designed as tubular hollow cylinders which converge (for example, when the sonotrode is formed in one piece) respectively are connected to each other (for example, when the individual elements are screwed together) in the crossing region. This preferably in such a way that through-openings are provided, accessible through both sleeves from both sides, and at the free end of the connecting portion a front opening is provided. However, this front opening may, for example for reasons of hygiene, be closed by a pin or the like. If the connecting portion is formed as a hollow cylinder, then the latter is, with regard to the wall thickness and/or the outside diameter and/or the length, preferably of similar dimensions as one or both of the sleeves.

A further preferred embodiment is characterized in that the first sleeve and the second sleeve have a symmetric mass distribution in particular with respect to a mirror plane spanned through the first axis and a plane normal to the sonotrode plane. This is preferably ensured, for example, by providing material thickenings and/or material recesses at the sonotrode in the crossing region to compensate for differences in length and/or diameter and/or inside diameter, or else also in the material of the two sleeves. Such thickenings can also be used to stabilize and/or they may be provided in the region of the free end of the connecting portion. The crossing region may also be formed as a separate block to which the connecting region and the two sleeves are formed on, or in which the two sleeves are screwed in. The crossing region can thus be designed, for example, for the attachment of different sleeves for different applications, the crossing region can also be used through its specific mass distribution to tare the vibration behavior of the sonotrode, so that at the end different sleeves designed as simple hollow cylinders can be screwed, which are no longer specifically designed for optimum vibration distribution, since this function is taken over by the design of the crossing region.

According to a further preferred embodiment, the sonotrode is made of an optionally coated metal material. This material is preferably selected from the group consisting of: aluminum, iron, titanium, steel, and principally containing these or largely composed of these alloys.

Generally, it is possible, as mentioned above, to design the sonotrode in one piece, for example from one of the above-mentioned materials. In this case the sonotrode is milled out, for example, from a work block. Alternatively, it is possible, as also mentioned above, to design the sonotrode from interconnected individual elements. The individual and interconnected elements can be, for example, the two sleeves, a crossing part and a connecting portion. The connection may preferably occur by form fit and/or force fit. A material fit is alternatively or additionally possible, but this should not adversely interact with the ultrasonic properties, which is the case in some of such connecting ways. Thus it is possible, for example, to design the sonotrode from interlocking threaded, inserted, crimped or riveted elements, in that the connecting portion and/or the crossing region and/or the first sleeve and/or the second sleeve are screwed together/inserted/compressed/riveted. For example, it is possible to design a crossing region in form of a block with three internal threads branching at the corresponding angles, so that subsequently the connecting portions formed as simple hollow cylinders with outer thread respectively sleeves can be screwed in the corresponding area. Preferably, the sonotrode is free of welds, as this may adversely affect the vibration behavior. As explained, coatings can be used, in particular coatings which, for example, influence the sliding properties, the properties of hygiene and/or the vibration transmission characteristics. Possible are, for example, especially in the area of the sleeves, plastic coatings such as PTFE.

Regarding sizing, in particular for amelioration of bores in the furniture industry, for example, or generally for the connection of porous materials such as wood, foams (metal foams, plastic foams, etc.), composites, or, also in the medical area, for example, when boring in the bone or porous tissue, it has been proven to be advantageous if the two sleeves have a length in the range of 5-50 mm, preferably in the range of 10-25 mm, and a diameter in the range of 2-15 mm, preferably in the range of 2.5-10 mm, in particular preferably in the range of 2.5-7 mm. As already mentioned above, it is advantageous if, for example, the dimensioning of the two sleeves with regard to the outside diameter is specifically designed for two standard bore diameters, conceivable is, for example, that a first sleeve has an outside diameter of 4.3 mm and a second sleeve an outside diameter of 3.5 mm.

Preferred pairs of sleeves are sized as follows:
combination of two small diameters 2.8 mm (outside diameter first sleeve) and 3.5 mm (outside diameter second sleeve) in a sonotrode;
combination of two large diameters 4.3 mm (outside diameter first sleeve) and 5.3 m (outside diameter second sleeve).

In principle, however, also other combinations can be implemented. To compensate for mass distribution, it is possible to slightly adjust the length, i.e., to design the sleeve with a thinner outside diameter slightly longer than that with thicker outside diameter. For the above two dimensions it is possible, for example, to design the sleeve with the outside diameter of 4.3 mm with a length of approximately 15 mm and that with an outside diameter of 3.5 mm with a length of 16 mm. The specific adjustment and balancing of the specific vibration behavior can usually be achieved largely with such a length adjustment of the sleeves, so that the optimization of the vibration characteristics can be relatively easily determined by experiments or simulations. An additional adjustment can be effected by the design of the crossing region, for example by material thickenings or recesses.

The corresponding through-opening through two such different sleeves can be of the same design with regard to the inside diameter so that the same guide pin can be used. However, it is also possible for the through-openings adjusted through the respective sleeves to be designed differently (for example, to maintain an optimal wall thickness), wherein when using different sleeves, also different guide pins must be used.

Preferably, at the first end of the connecting portion an interface for attachment to the ultrasonic vibration transducer is provided, preferably in the form of a form fit and/or force fit coupling region, and in particular preferably in the form of a thread, a flange, a groove or a bayonet catch.

Furthermore, the present invention relates to a sonotrode tool with an ultrasonic vibration transducer and a sonotrode as detailed above, wherein preferably the vibration transducer comprises a converter formed as a handle, as well as a booster, wherein the sonotrode is fixed to the booster and is designed integrally therewith. An appropriate tool typically also has an electrical connection and a control with which the applied vibration can be adjusted. Typically vibrations in the range of 20-120 kHz are applied, preferably in the range of 30-80 kHz, more preferably in the range of 50-80 kHz.

Such sonotrode tool is preferably characterized in that it is designed as a hand tool for the medical area, especially for the area of implants, particularly for the dental area.

Furthermore, the present invention relates to the use of such a sonotrode or of such a sonotrode tool for the amelioration of a recess, especially in the framework of a method, such as described in detail in WO 2009/141252. It may be a medical method or a non-medical method. Regarding method, accordingly, the disclosure content of WO 2009/141252 is expressly included in this disclosure. It is, in other words, a method of amelioration of a recess in a porous, foraminous, and through the recess exposed with hollow spaces material, wherein one of the two cylindrical sleeves comprising a cylindrical lateral surface having an outside diameter and having a central recess for accommodating a guide pin is used, wherein the guide pin is provided to be inserted substantially down to the base of the recess before applying mechanical energy, wherein the guide pin in the region of the end thereof facing the base of the recess is surrounded by an amelioration collar made from a material that can be liquefied by way of mechanical energy, wherein the cylindrical lateral surface of the amelioration collar substantially has the same outside diameter as the sleeve, and wherein the guide pin is accommodated in the central recess in a displaceable manner such that the sleeve upon applying mechanical energy can be displaced relative to the guide pin in the direction toward the base of the recess while liquefying and laterally and/or longitudinally displacing the material of the amelioration collar.

Further embodiments are defined in the dependent claims.

BRIEF DESCRIPTION OF THE DRAWINGS

Preferred embodiments of the invention are described below on the basis of the drawings, which are illustrative only and are not to be interpreted in a restrictive way. The drawings show:

FIG. 5 a sonotrode in a perspective representation; and

FIG. 6 possible dimensionings of a sonotrode.

DESCRIPTION OF PREFERRED EMBODIMENTS

Particularly in the medical area, notably for the implant area, and especially for the area of dental implants, a method for amelioration of recesses in porous materials is known, for example from WO 2009/141252. In this case, a substantially cylindrical collar of a material liquefied under ultrasound is used to fill in a liquefying way the pores of the wall areas of the recess with this material under the effect of ultrasound. This is done so that a guide pin, which is guided in a sleeve with a respective axial recess, is inserted into an already provided bore as a guide element, and then the thereon slide-mounted sleeve is pushed down toward the base of the recess. Around the guide pin in the tip region a hollow cylinder of a liquefiable material is provided, and that is displaced by the sleeve, which has an outer circumference which corresponds substantially to the inside diameter of the bore to be ameliorated, by the downward shifting and simultaneous liquefying of this material collar outwards into the porosity and accordingly fills voids in the material.

In connection with such a method it is advantageous when an ultrasonic vibration is applied only to the sleeve which is guided on the guide pin, so that the material to be liquefied is liquefied in each case only where it is in contact with this sleeve. Furthermore, lateral ultrasonic vibrations at this sleeve should be avoided, that is, the ultrasonic vibrations should extend along the axis of this sleeve. Since the space is cramped especially in the dental field, accordingly there is a need for devices which are capable to deflect the ultrasonic vibration of a hand-held device in one direction, so that it can then be optimally used in a machining of a bore. Such a device will be described hereafter.

Figure 1:
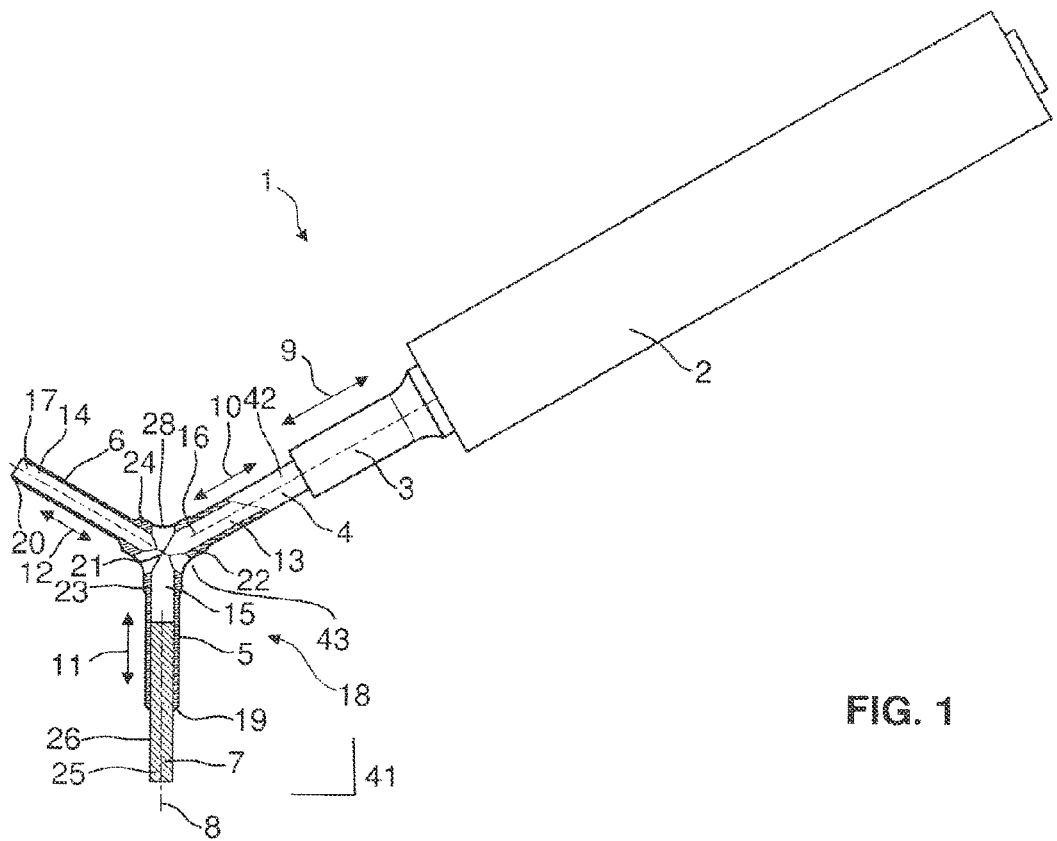
FIG. 1 on a lateral view a sonotrode tool, in which the sonotrode is represented partially axially cut and is located in the paper plane, and wherein the guide pin projects from front of the first sleeve.

FIG. 1 shows a lateral view of a sonotrode tool 1 with a handle in the form of a converter 2, in which the actual ultrasound is generated. The ultrasound is applied at a frequency in the range of, for example, 30 to 70 kHz and the amplitude is about 1-5 micrometers, the ultrasonic vibration extends in an axial direction, as is indicated schematically by the arrow 9. The ultrasonic vibration is first transferred to a so-called booster 3, in which the amplitudes are amplified so that the ultrasonic vibrations then in the area of the actual sonotrode 18 have an amplitude in the range between 5-25 micrometers.

At this booster 3, the actual sonotrode element 18 is attached. This occurs, for example, via a coupling point in the form of a thread, but also other coupling possibilities are conceivable. The actual sonotrode 18 has a cylindrically shaped connecting portion 4, which in this case is formed as a hollow cylinder, that is, it has an internal cavity 13 extending along the axis 16. This cavity is open towards the front, that is, there is a front opening 31.

At the free front end of the connecting portion of the sonotrode 18, a crossing region 36 is located. At this crossing region 36, the sonotrode 18 branches into two sleeves pointing in different directions, a first sleeve 5 with a larger outside diameter and a second sleeve 6 with a smaller outside diameter. The two portions 5 and 6 branch off symmetrically, that is, the axis 8 of the first sleeve 5, and the axis 17 of the second sleeve 6 together form an angle of 120 degrees, said axes again in turn an equal angle with the aforementioned axis 16 of the connecting portion 4, and the individual arms of this tripod are all in a common plane which is indicated schematically by reference numeral 41 and which is located in this representation in the paper plane.

Both the first sleeve 5 and the second sleeve 6 are designed as hollow cylinders, that is, they each surround a cavity 15 respectively 14. This cavity is designed as a through-opening through the entire sonotrode area, i.e. at the front end of the first sleeve there is a front opening 27 and on the rear a rear opening 28, and at the second sleeve 6 there is also a front opening 29 and a rear opening 30 (see also FIG. 2). In these respective through-openings, which have a constant inside diameter over the total length, a guide pin 7 can be inserted by sliding. If an ultra-vibration is applied over the booster 3 in the axial direction as according to arrow 9, this also results in an axial ultrasonic vibration in the connecting portion 4, as schematically indicated by the arrow 10. As a result of the symmetrical design of the two arms 5 respectively 6, this axial vibration is divided into two axial vibrations in each sleeve, as is represented by arrows 11 and 12. This is entirely in keeping with the considerations of symmetry, such as are known, for example, from the vibration behavior of molecules with similar symmetry group. If the sonotrode 18 is designed completely symmetrically, that is, both the sleeves 5 and 6 are designed of the same length, of the same wall thickness and of the same material and with the same diameter, then the vibration distributes respectively axially uniformly on the two sleeves 5 and 6 and also extends in these sleeves, in particular when the respective arms form an angle of 120 degrees, along the respective axis.

Since, however, at the same time, the purpose is to ensure that the two arms of the sleeves 5, 6 can be used for different applications, that is, can be used with different outside diameter for bores with different diameters, this complete symmetry is specifically not given here, however, this fact is taken into account to ensure a truly pure axial vibration in the respective arm, by, on one hand, designing the sleeve portion 6 with the smaller diameter slightly longer than the shorter sleeve portion 5 with the larger diameter, and by providing additional material thickenings 24 on the arm 6 in the crossing region, and corresponding material thickenings in the area 23 at element 5. Thus, the vibration characteristics can be balanced and it can be ensured that only the axial vibrations shown by the arrows in FIG. 1 are actually applied to the individual arms.

To implement the initially mentioned method according to WO 2009/141252, additionally the encircling edge of the respective sleeve 5, 6 at the tip, i.e., the distal edge 19, has a conically tapered form to ensure a highly concentrated lateral displacement of a material sleeve consisting of a liquefiable material, which is pushed out on a guide pin 7.

Figure 2:
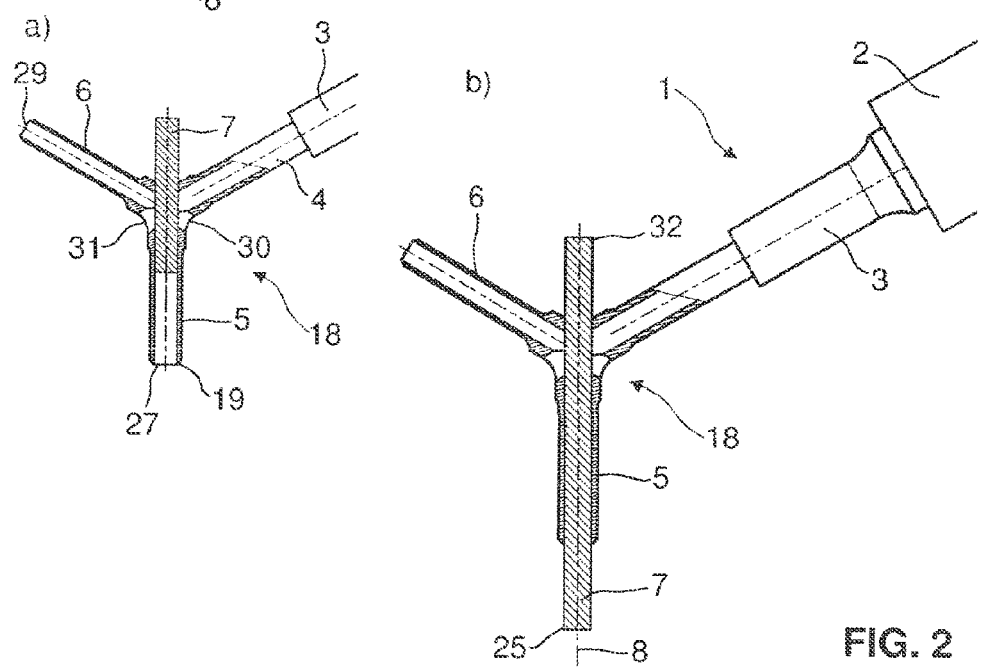
FIG. 2 in a) in a lateral view the sonotrode according to FIG. 1, wherein the guide pin projects from the rear of the first sleeve, and in b) a sonotrode tool according to FIG. 1 with a long guide pin, which projects on both sides from the first sleeve.

FIG. 2 shows how the guide pin 7 can be pushed through the central through-opening in the sleeve 5, in FIG. 2a it is pushed backwards, in FIG. 2b a long guide pin is provided which extends through the entire through-opening and which, in other words, protrudes with its rear end 32 to the rear. Guide pins 7 can also be provided according to needs in different length and can, for example, be made of a plastic material.

Figure 3:
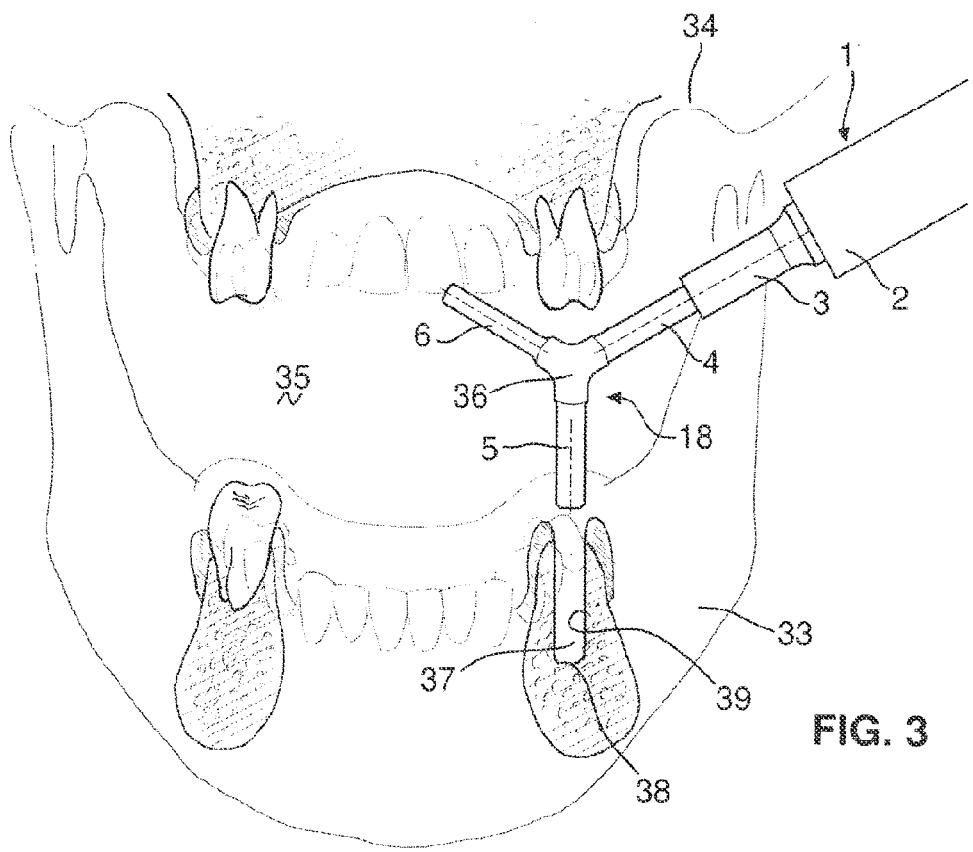
FIG. 3 a schematic perspective view of a sonotrode tool inserted in a mouth opening above a prepared bore in the lower jaw.

FIG. 3 shows a schematic representation of the use of such a sonotrode tool in the dental field, i.e. where in a lower jaw 33 a prepared bore 37 is provided, which comprises a lateral peripheral porous wall region 39. In a method according to WO 2009/141252 now a guide pin (not illustrated here) is inserted in the bore, and at the end projecting into the bore an encircling material collar of material liquefying under the effect of vibrations is provided. The sleeve 5 is shifted inside in a downward movement in FIG. 3 successively into the bore, so that the hollow cylindrical material collar is liquefied in the contact region with the distal end of the sleeve successively from top to bottom and laterally displaced in the porous region 39, while the guide pin remains stationary.

Figure 4:
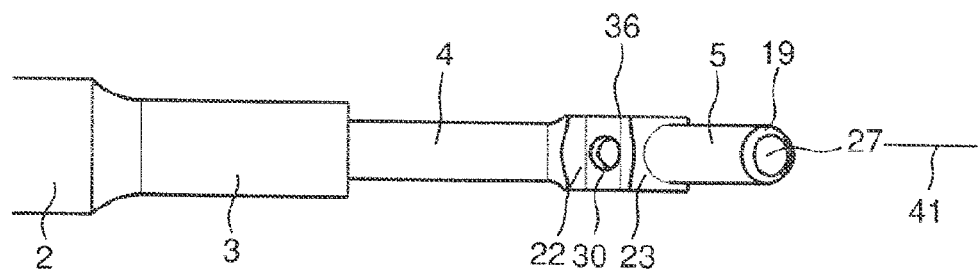
FIG. 4 a sonotrode in a representation along the sonotrode plane on the first sleeve.

FIGS. 4 and 5 show perspective views of such a sonotrode; here it is recognizable how the crossing region 36 may be designed in the form of a block, whose design in particular may also be adapted to the vibrational conditions. FIG. 6 shows a possible dimensioning and design of such a sonotrode, there is, for example, a possible length L of the first sleeve 5 in the range of 10-20 mm, for example approximately 15 mm, the outside diameter D is, for example, 4.3 mm, and the inside diameter Di is 3 mm so that a guide pin 7 could be used with an outside diameter of 3 mm. Accordingly, a material collar of liquefiable material with an inside diameter of 3 mm and an outside diameter of 4.3 mm could be used.

As described above, the second sleeve 6 has, in turn, for the balancing of the vibrations, a slightly longer length l in the range of 10-20 mm, here specifically approximately 16 mm, the outside diameter d is 3.5 mm and the inside diameter is 2.5 mm. Thus, when this sleeve is used for a smaller bore with an outside diameter of 3.5 mm, a guide pin 7 with an outside diameter of 2.5 mm is used. Accordingly, a material collar of liquefiable material with an inside diameter of 2.5 mm and an outside diameter of 3.5 mm would be used.

As already shown in the previous figures, also the connecting portion 4 is formed as a hollow cylinder, that is, it surrounds a cavity. This portion typically has a length k which is approximately equal to the length of each sleeve. In the specific case shown here, this portion has a length k of approximately 15 mm. The three arms form each angle α, β, γ, these angles in the specific example represented here are all 120 degrees.

LIST OF REFERENCE NUMERALS

1 Sonotrode tool
2 Converter
3 Booster
4 Connecting portion of 18
5 First connecting portion of 18, first sleeve with large diameter
6 Second connecting portion of 18, second sleeve with small diameter
7 Guide pin
8 Axis of 5, second axis
9 Vibration direction in 3
10 Vibration direction at 4
11 Vibration direction at 5
12 Vibration direction at approximately six
13 Cavity in 4
14 Cavity in 6
15 Cavity in 5
16 Axis of 4, first axis
17 Axis of 6, third axis
18 Sonotrode
19 Distal edge of 5
20 Distal edge of 6
21 Crossing point of the elements 4-6
22 Material thickenings in the area of the crossing region at 4
23 Material thickenings in the area of the crossing region at 5
24 Material thickenings in the area of the crossing region at 6
25 Free distal end of 7
26 Cylindrical peripheral surface of 7
27 front opening of 5
28 Rear opening of 5
29 Front opening of 6
30 Rear opening of 6
31 Front opening
32 Rear end of 7
33 lower jaw
34 upper jaw
35 Mouth opening
36 Crossing region of 18
37 Prepared bore in 33
38 Base of 37
39 Porous wall region of 37
40 Fixing opening for 18 in 3
41 sonotrode plane
42 Rear end of 4, connection side of 4
43 Free end of 4
α Opening angle between 8 and 17, respectively 5 and 6
β Opening angle between 16 and 17, respectively 4 and 6
γ Opening angle between 8 and 16, respectively 4 and 5, first angle
L Length of work section of 5
D Outside diameter of 5
Di Inside diameter of 5
l Length of work section of 6
d Outside diameter of 6
di Inside diameter of 6
k Length of 4 between 3 and 36

The invention claimed is:

1. A sonotrode for connection to an ultrasonic vibration transducer comprising
a connecting portion, which extends along a first axis and is attachable or connectable at a first end of said connecting portion to the vibration transducer, wherein the connecting portion is made to vibrate almost exclusively along the first axis by the ultrasonic vibration transducer,
wherein
at a free end of said connecting portion opposite from the first end, in a common crossing region, both
a substantially cylindrical, first sleeve, which extends along a second axis, and
a substantially cylindrical, second sleeve, which extends along a third axis, are arranged,
wherein said first axis forms a first angle in the range of 100-140° with said second axis, wherein said first axis forms a second angle in the range of 100-140° with said third axis, and wherein the three axes are arranged substantially in one sonotrode plane.

2. The sonotrode according to claim 1, wherein a ratio of an outside diameter of the first sleeve to a length of the first sleeve along the second axis is in the range of 1:2-1:10, and wherein a ratio of an outside diameter of the second sleeve to a length of the second sleeve along the third axis is in the range of 1:2-1:10.

3. The sonotrode according to claim 1, wherein the first angle and/or the second angle is/are in the range of 110-130°.

4. The sonotrode according to claim 1, wherein the first angle and the second angle are the same up to a deviation of not more than 5°.

5. The sonotrode according to claim 1, wherein both the first sleeve and the second sleeve are designed as a circular cylinder with a circular cylindrical outer surface, and wherein an outside diameter of the first sleeve is greater than an outside diameter of the second sleeve.

6. The sonotrode according to claim 1, wherein the first sleeve, the second sleeve, or both, has a central axial cylindrical recess, which is open to a respective free end to form a front opening.

7. The sonotrode according to claim 1, wherein the connecting portion and the first sleeve and the second sleeve are designed as tubular hollow cylinders, which converge and are connected to each other in the crossing region, and wherein the first sleeve and the second sleeve each have a through-opening, each through-opening being accessible from both sides of a sleeve.

8. The sonotrode according to claim 1, wherein the first sleeve and the second sleeve have a symmetrical mass distribution, with respect to a mirror plane arranged through the first axis and a plane normal to the sonotrode plane, wherein, for compensating for differences in at least one of a length, a diameter, an inside diameter, material thickenings, and material between the first and second sleeve, recesses are formed in the crossing region.

9. The sonotrode according to claim 1, wherein the sonotrode is made of a metallic material.

10. The sonotrode according to claim 1, wherein the first sleeve and the second sleeve each have a length in the range of 5-50 mm and a diameter in the range of 2-15 mm.

11. A sonotrode tool with an ultrasonic vibration transducer and a sonotrode according to claim 1, wherein the vibration transducer comprises a handle-shaped converter and a booster, wherein the sonotrode is fixed to the booster.

12. The sonotrode tool according to claim 11, wherein the sonotrode tool is designed as a hand tool for a medical area.

13. The sonotrode tool according to claim 11, wherein the sonotrode tool is designed as a hand tool for an area of implants, including a dental area.

14. A method of using a sonotrode according to claim 1, or of using a sonotrode tool with an ultrasonic vibration transducer and said sonotrode for the amelioration of a recess, the recess being in a porous material, in a foraminous material, or in a material with hollow spaces which are exposed due to the recess,
wherein the vibration transducer comprises a handle-shaped converter and a booster,
wherein the sonotrode is fixed to the booster or is designed integrally with the booster,
wherein at least one of said first cylindrical sleeve or said second cylindrical sleeve has a cylindrical outer surface with an outside diameter and a central recess for accomodating a guide pin,
wherein the guide pin is provided to be inserted substantially down to a base of the recess before applying mechanical energy,
wherein the guide pin in the region of an end thereof facing the base of the recess is surrounded by an amelioration collar made from a material that can be liquefied by way of mechanical energy,
wherein a cylindrical outer surface of the amelioration collar substantially has the same outside diameter as the sleeve, and
wherein the guide pin is accommodated in the central recess in a displaceable manner such that the sleeve upon applying mechanical energy can be displaced relative to the guide pin in the direction toward the base of the recess while liquefying and laterally and/or longitudinally displacing the material of the amelioration collar.

15. The sonotrode according to claim 1, wherein a ratio of the outside diameter of the first sleeve to the length of the first sleeve along the second axis is in the range of 1:3-1:6 and a ratio of the outside diameter of the second sleeve to the length of the second sleeve along the third axis is in the range of 1:3-1:6.

16. The sonotrode according to claim 1, wherein the first angle and/or the second angle is/are in the range of 118-122°.

17. The sonotrode according to claim 1, wherein the first angle, defined between said first axis and said second axis, and the second angle, defined between said first axis and said third axis, are the same up to a deviation of not more than 2°, and wherein the second axis and the third axis define a third angle, which lies in the range 105-125°.

18. The sonotrode according to claim 1, wherein both the first sleeve and the second sleeve are designed as a circular cylinder with a circular cylindrical outer surface, and wherein an outside diameter of the first sleeve is 1.2-2 times greater than an outside diameter of the second sleeve, and wherein a first ratio of an outside diameter of the first sleeve to a length of the first sleeve along the second axis and a second ratio of the outside diameter of the second sleeve to a length of the first sleeve along the third axis are substantially the same.

19. The sonotrode according to claim 1, wherein at least one of the first sleeve and the second sleeve has a central axial cylindrical recess, which is open to a respective free end to form a front opening, wherein an encircling edge of each sleeve formed in an area of said front opening is designed conically tapered, and wherein the recess is a through-bore with a constant inside diameter which is accessible at a respective position of the crossing region through a respective rear opening.

20. The sonotrode according to claim 1, wherein the connecting portion and the first sleeve and the second sleeve are each designed as tubular hollow cylinders, which converge and are connected to each other in the crossing region, and wherein the first sleeve and second sleeve each have a through-opening, each through-opening being accessible from both sides of each sleeve and wherein at the free end of the connecting portion a front opening is provided, which can be closed by a closing element.

21. The sonotrode according to claim 1, wherein the first sleeve and the second sleeve have a symmetrical mass distribution, wherein, for compensating for differences in at least one of the length, the diameter, the inside diameter, material thickenings, and material between the first and second sleeve, recesses are formed in the crossing region.

22. The sonotrode according to claim 1, wherein the sonotrode comprises a metallic material, selected from the group consisting of: aluminum, iron, titanium, steel, and alloys thereof.

23. The sonotrode according to claim 1, wherein the sonotrode is formed in one piece and machined from a single work block, or wherein the sonotrode is formed by threaded elements screwed together, at least two of the connecting portion, the crossing region/, the first sleeve, and the second sleeve being screwed together.

24. The sonotrode according to claim 1, wherein the first sleeve and the second sleeve have a length in the range of 10-25 mm and a diameter in the range of 2.5-7 mm.

25. The sonotrode according to claim 1, wherein at the first end of the connecting portion an interface for attachment to the ultrasonic vibration transducer is provided, in the form of a thread, a flange, a groove or a bayonet catch.

* * * * *